United States Patent [19]
Fischell et al.

[11] Patent Number: 5,669,932
[45] Date of Patent: Sep. 23, 1997

[54] MEANS FOR ACCURATELY POSITIONING AN EXPANDABLE STENT

[75] Inventors: Robert E. Fischell, Dayton, Md.; Michael E. Kopp, Burlingame, Calif.

[73] Assignee: IsoStent, Inc., Belmont, Calif.

[21] Appl. No.: 654,990

[22] Filed: May 29, 1996

[51] Int. Cl.$^6$ .................................................. A61M 29/00
[52] U.S. Cl. ........................................ 606/198; 191/108
[58] Field of Search ............... 604/96–104; 606/106, 606/108, 191–200

[56] References Cited

U.S. PATENT DOCUMENTS

| | | | |
|---|---|---|---|
| 5,201,901 | 4/1993 | Harada | 606/198 |
| 5,484,444 | 1/1996 | Braunschweiler et al. | 606/108 |

*Primary Examiner*—Glenn Dawson

[57] ABSTRACT

One aspect of the present invention envisions two radiopaque marker bands located within the balloon of the balloon angioplasty catheter for balloon expandable stents, or located at a distal portion of a stent delivery catheter designed for self-expanding stents. When the balloon is expanded to its nominal diameter, the proximal marker band (of the two bands) is positioned to indicate the proximal extremity of the stent and the distal marker band is used to indicate the distal extremity of the stent. A second aspect of this invention envisions one or more radiopaque marker bands placed onto a distal portion of a stent delivery catheter with each radiopaque marker band indicating the position of a special expandable cell of the stent, which cell can be placed at the ostium of a side branch artery where that side branch enters into a main artery. The interventionalist would align such a radiopaque marker band with the ostium of the side branch prior to stent deployment. After stent deployment, the balloon of a balloon angioplasty catheter would be inserted through the special cell of the stent and into the side branch. The balloon would then be inflated to high pressure so as to open that special stent cell where the struts of that cell would otherwise block the flow of blood into that side branch.

6 Claims, 5 Drawing Sheets

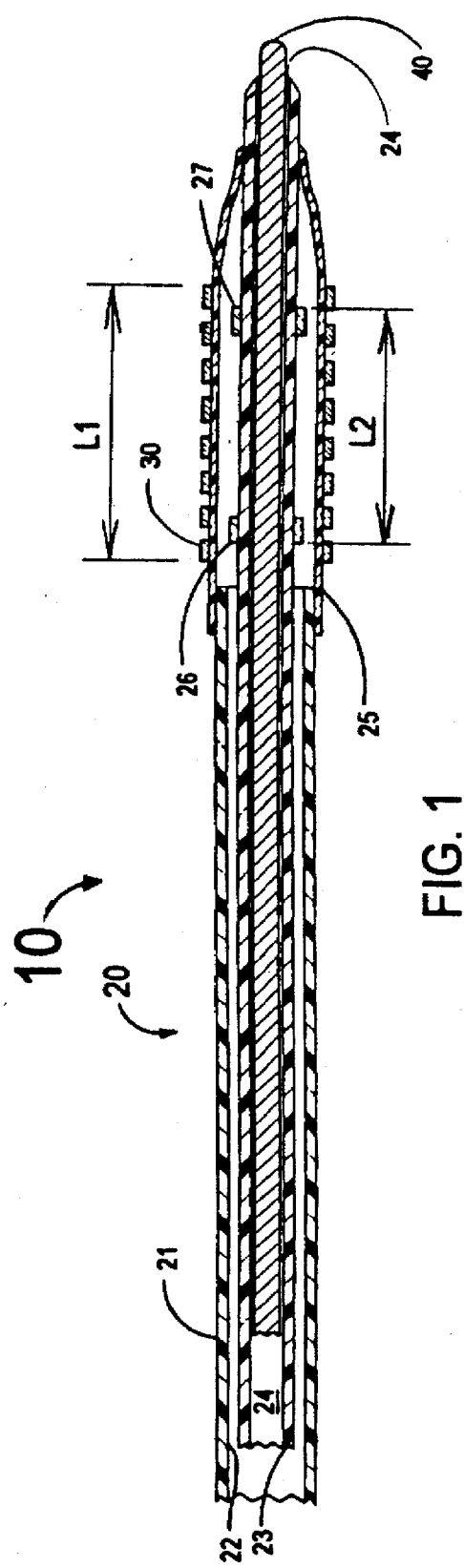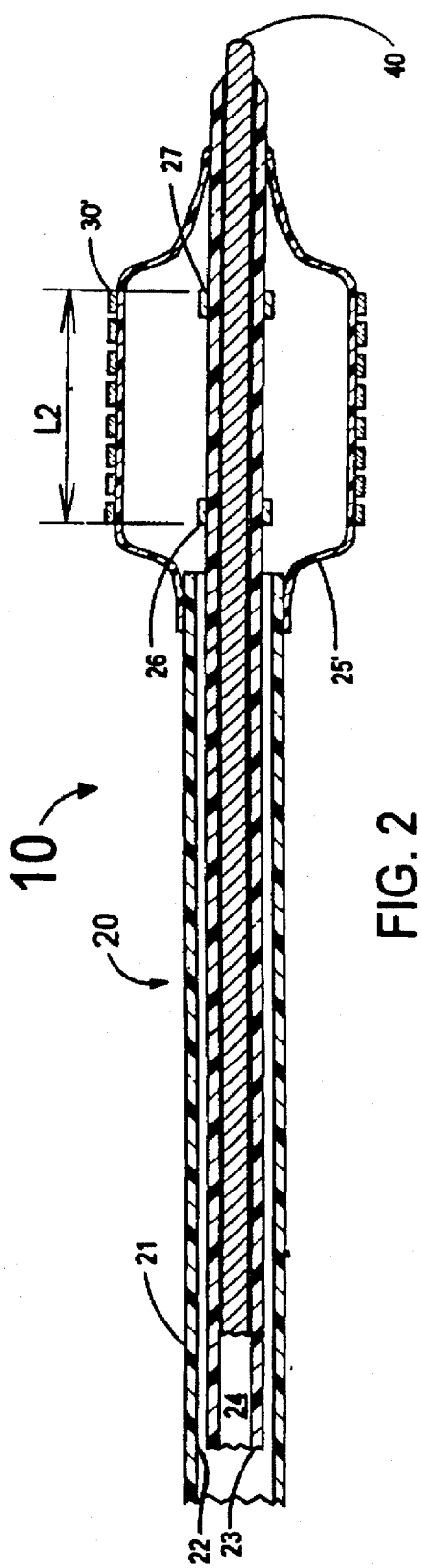

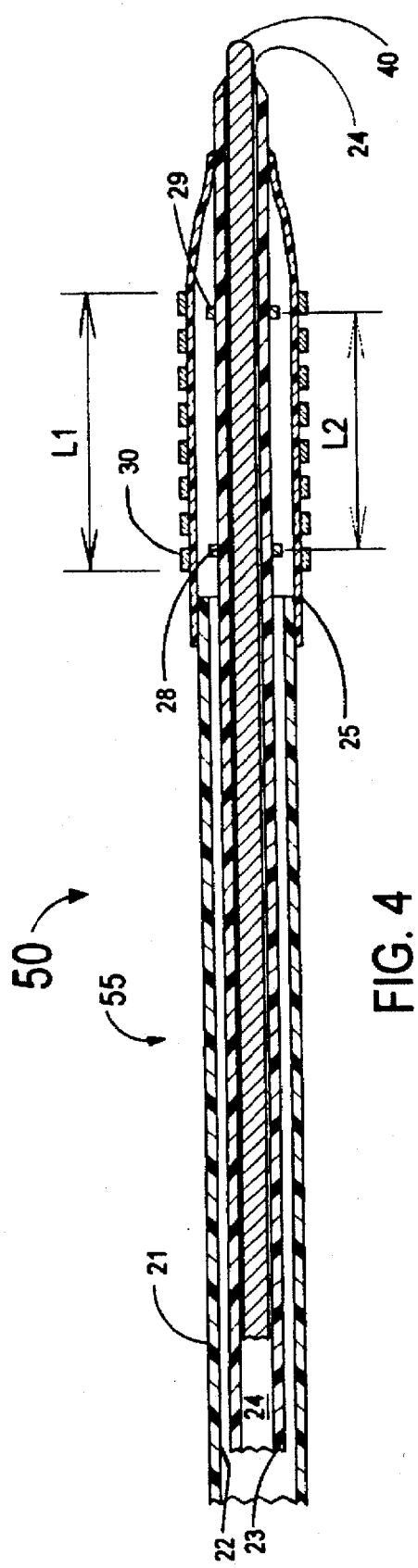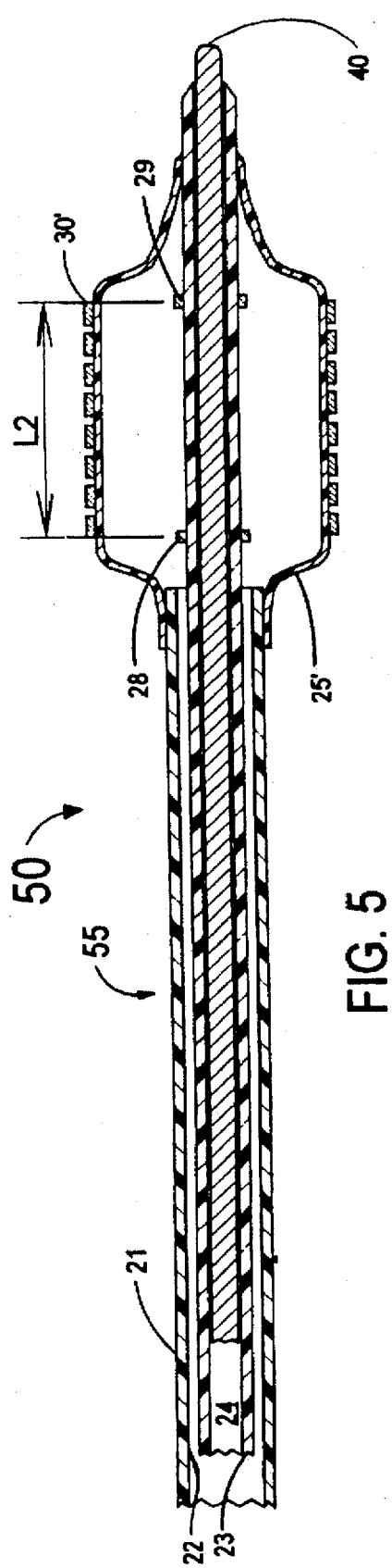

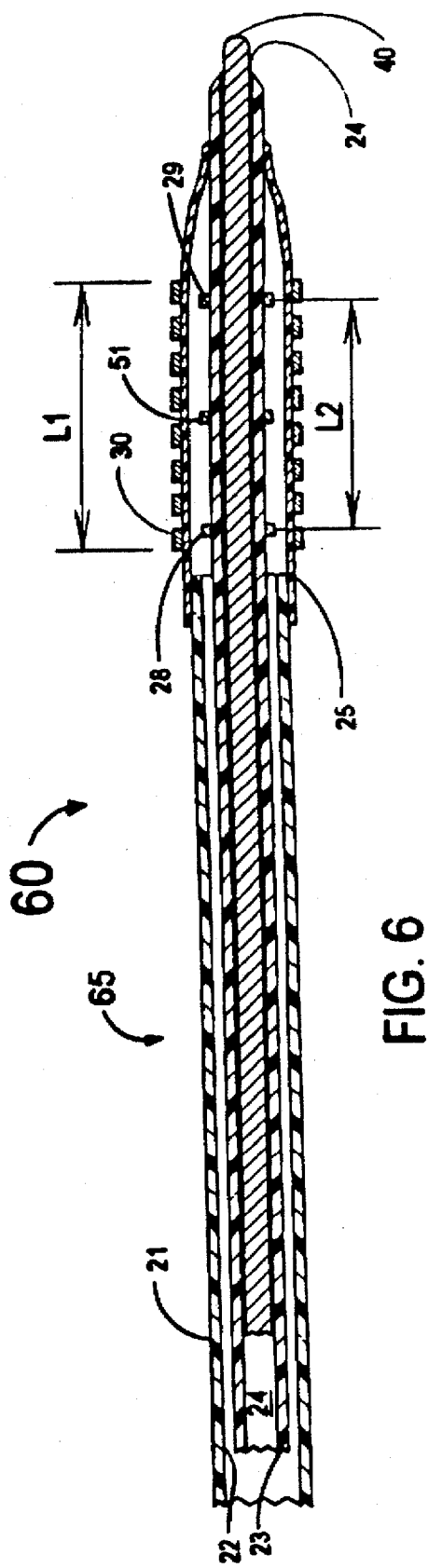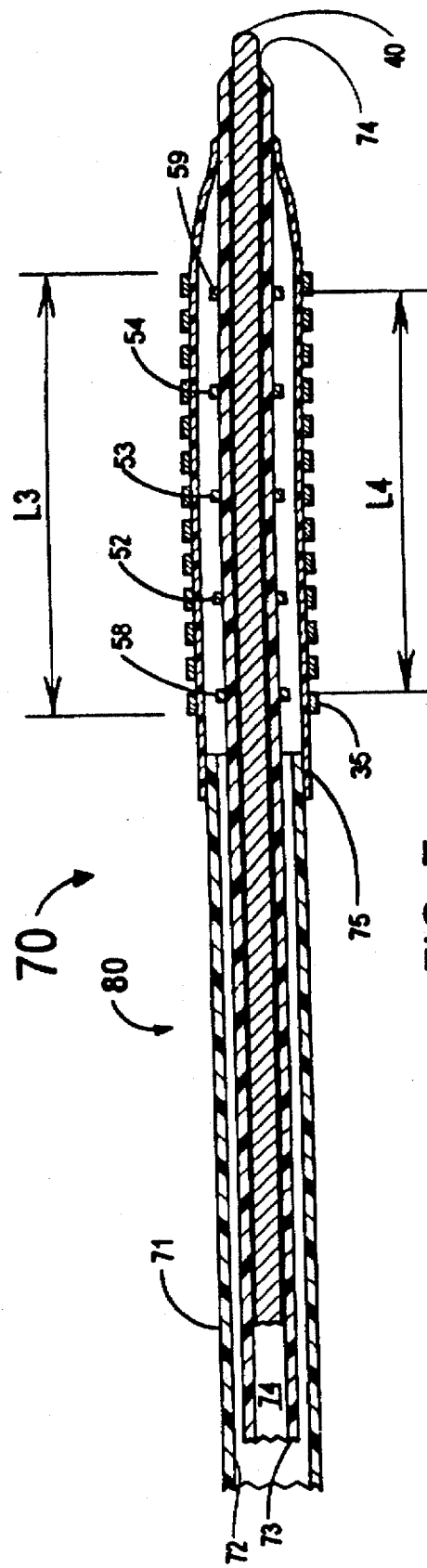

MEANS FOR ACCURATELY POSITIONING AN EXPANDABLE STENT

FIELD OF USE

This invention is in the field of stents for placement within vessels of the human body.

BACKGROUND

Expandable stents are currently being used for maintaining patency of many different vessels of the human body. A typical vascular stent would be placed onto a distal portion of a balloon angioplasty catheter. A single radiopaque marker located at the center of the balloon of the balloon angioplasty catheter is typically used to center the stent at the center of a lesion in the vessel. A frequently treated lesion is a stenosis in a coronary artery. An important objective of the interventional physician is to have the length of the stenosis fully covered by the length of the deployed stent. However, stents often shorten considerably as a function of the final diameter to which they are expanded. Therefore, when there is only a single, centrally located marker band, the interventional physician has to guess if the deployed length of a stent will be adequate to cover a particular length of a stenosis.

When a stent is placed in an ostial or bifurcation stenosis, it is important to position the stent's proximal end exactly at the vessels mouth without having the stent extend for any length into the main artery. With only a single radiopaque marker band placed on the balloon at the longitudinal center of the stent, it is very difficult to accomplish that objective.

It is anticipated that some stents will have special expandable cells that can be placed at the ostium of a side branch of a main artery. Such cells could then be balloon expanded to form an opening that is larger than the diameter of the side branch at its ostium. Thus, the flow of blood into such a side branch would not be impeded by any strut or wire of the stent. Furthermore, a stent strut placed across the ostium of a side branch creates what has been termed "stent jail". Such a "stent jail" can prevent the introduction of another expandable stent into that side branch. No existing stent delivery catheter and stent system includes a radiopaque marker that indicates the position of such a special expandable stent cell so that the stent can be accurately aligned with the ostium of the side branch prior to stent deployment.

SUMMARY OF THE INVENTION

One aspect of the present invention envisions two radiopaque marker bands located within the balloon of the balloon angioplasty catheter for balloon expandable stents, or located at a distal portion of a stent delivery catheter designed for self-expanding stents. When a balloon expandable stent is deployed to its nominal diameter, the proximal marker band (of the two bands) is positioned so as to indicate the proximal extremity of the stent and a distal marker band is used to indicate the distal extremity of the stent. If the stent is self-expanding, a proximal marker band and a distal marker band on a different style of stent delivery catheter could be used to indicate the deployed proximal and distal extremities of such a self-expanding stent. It should be noted that the "nominal" diameter of an expanded balloon or stent is the diameter that the manufacturer indicates on the package in which that balloon or stent is placed. For example, a "nominal" balloon diameter of 3.0 mm will occur at a nominal inflation pressure of, let us say, 10 atmospheres. But at 16 atmospheres the balloon diameter would be 3.2 mm, which is not the balloon's nominal diameter.

A second aspect of this invention envisions one or more radiopaque marker bands placed onto a distal portion of a stent delivery catheter with each radiopaque marker band indicating the position of a special expandable cell of the stent, which cell can be placed at the ostium of a side branch artery where that side branch enters into a main artery. The interventionalist would align such a radiopaque marker band with the ostium of the side branch prior to stent deployment. After stent deployment, the balloon of a balloon angioplasty catheter would be inserted through the special cell of the stent and into the side branch. The balloon would then be inflated to high pressure so as to open that special stent cell where it would otherwise block the flow of blood into that side branch.

Thus it is an object of this invention to have a stent delivery catheter that utilizes proximal and distal marker bands that indicate the extremities of the stent after it is deployed.

Another objective of this invention is to provide a stent delivery catheter which has proximal and distal radiopaque marker bands which can be used for implanting self-expanding stents into a vessel of the human body. The radiopaque marker bands being adapted to indicate the extremities of the stent after it is deployed.

Still another objective of this invention is to provide a set of balloon angioplasty catheters having several different nominal balloon diameters wherein each balloon angioplasty catheter has a specific separation distance between a proximal marker band and a distal marker band which separation distance corresponds to the proximal and distal extremities of a stent when expanded to that specific nominal balloon diameter.

Still another object of this invention is to provide one or more radiopaque marker bands placed onto a distal portion of a balloon angioplasty catheter onto which the stent is mounted, with the longitudinal position of each radiopaque marker band corresponding to the longitudinal position of a special expandable cell of the stent which cell can be placed at the ostium of a side branch artery and then that cell can be balloon expanded to provide an unobstructed opening to allow unimpeded blood flow into that side branch.

These and other important objects and advantages of this invention will become apparent from the detailed description of the invention and the associated drawings provided herein.

BRIEF DESCRIPTION OF THE DRAWINGS

FIG. 1 is a longitudinal cross section of a distal portion of a stent delivery catheter including a balloon expandable stent shown in its pre-deployed diameter and its pre-deployed length L1; this stent delivery catheter includes two comparatively long radiopaque marker bands whose proximal and distal extremities are separated by a length L2.

FIG. 2 is longitudinal cross section of the distal portion of the stent delivery catheter of FIG. 1 with the stent expanded to its pre-determined, nominal diameter and the stent shortened to a length L2 where L2<L1.

FIG. 4 is a longitudinal cross section of a distal portion of a stent delivery catheter including a balloon expandable stent shown in its pre-deployed diameter and its pre-deployed length L1; this stent delivery catheter includes two comparatively short radiopaque marker bands, the centers of the radiopaque marker bands being separated by a length L2.

FIG. 5 is longitudinal cross section of the distal portion of the stent delivery catheter of FIG. 4 with the stent expanded to its pre-determined, nominal diameter and the stent has shortened to a length L2 where L2<L1.

FIG. 6 is a longitudinal cross section of a distal portion of a stent delivery catheter including a balloon expandable stent shown in its pre-deployed diameter and its pre-deployed length L1; this stent delivery catheter includes three radiopaque marker bands, the outer two radiopaque marker bands being separated by a length L2 which is equal to the length of the stent when expanded to its nominal diameter, and a third radiopaque marker band which indicates the center of a group of one or more special expandable cells of the stent which cells can be placed at a side branch of a main artery into which the stent can be fully deployed.

FIG. 7 is a longitudinal cross section of a distal portion of a stent delivery catheter including a balloon expandable stent shown in its pre-deployed diameter and its pre-deployed length L1; this stent delivery catheter includes five radiopaque marker bands, the outer two radiopaque marker bands being separated by a length L2 which is equal to the length of the stent when expanded to its nominal diameter, and the other three radiopaque marker band, indicating the center of three separated groups of one or more special cells of the stent, any of the three special cells being able to be placed at a side branch of a main artery into which the stent can be fully deployed.

DETAILED DESCRIPTION OF THE DRAWINGS

Figure 3:
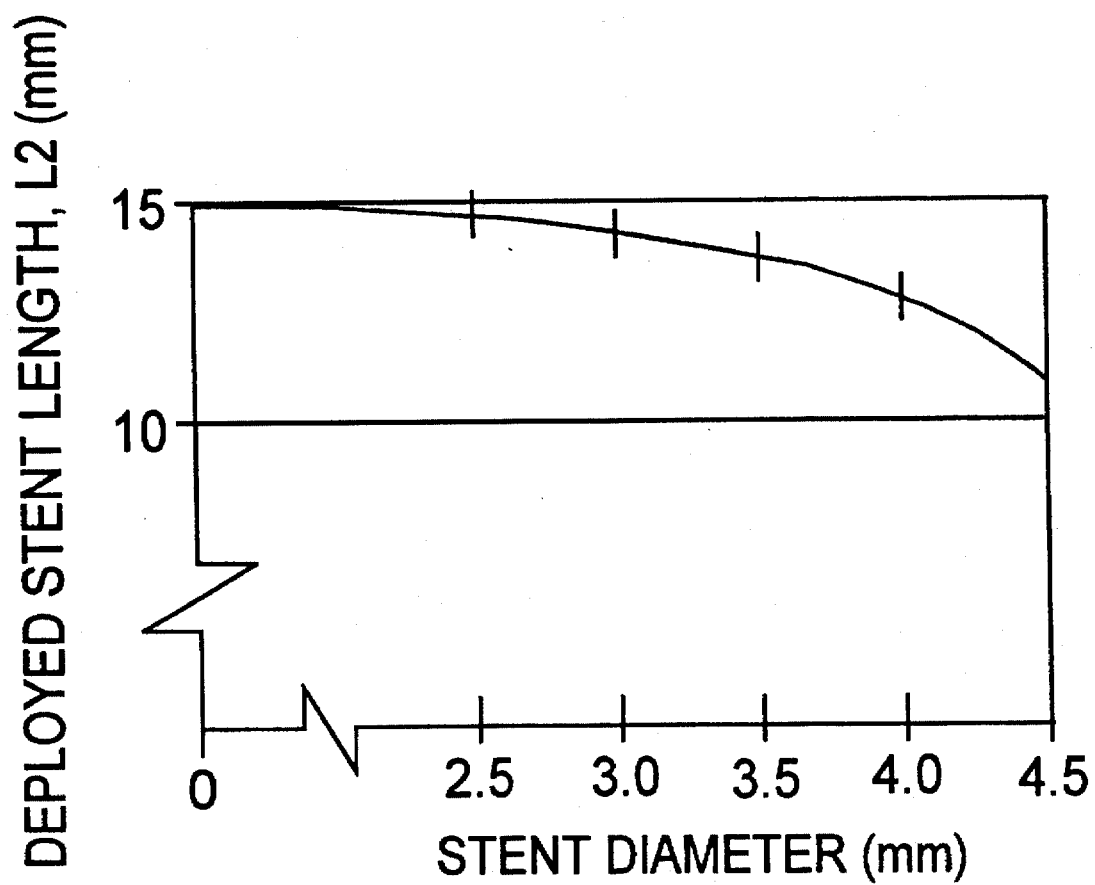
FIG. 3 is a graph showing a typical relationship of diameter vs. length for a balloon expandable stent.

FIG. 1 shows a typical balloon angioplasty catheter plus stent system 10 that is used to place a balloon expandable stent 30 into a vessel of a human body. The system 10 consists of a balloon angioplasty catheter 20, a stent 30 and a guide wire 40. The balloon angioplasty catheter 20 has an outer shaft 21 and an inner shaft 23. Between the outer shaft 21 and the inner shaft 23 is an annular passageway 22 through which a liquid is passed to inflate or deflate the balloon 30. The inner shaft 23 has a central lumen 24 through which a guide wire 40 can be passed. The proximal end of the balloon 25 is adhesively bonded to the distal end of the outer shaft 21, and the distal end of the balloon 25 is adhesively bonded onto a distal portion of the inner shaft 23. A proximal radiopaque marker band 26 and a distal radiopaque marker band 27 are each adhesively joined to an outer surface of the inner shaft 23. The predeployed length of the stent 30 is L1 and the separation length between proximal end of the band 26 and the distal end of the band 27 is L2.

FIG. 2 shows the balloon 25' expanded to its nominal diameter which causes the radially outward expansion of the stent 30' which expansion causes the stent 30' to shorten to a length L2. Thus, the extremities of the marker bands 26 and 27 and the extremities of the deployed stent 30' each has the same separation length L2. Although the marker bands 26 and 27 are shown to be completely within the dimension L2, each of them could be centered at L1 (as shown in FIG. 4) or have L1 be the dimension to the distal end of the proximal marker and the proximal end of the distal marker.

FIG. 3 shows a typical curve of stent length as a function of the deployed diameter of the balloon 25'. A typical stent could have a pre-deployment length L1=15 mm and its post-deployment length at a diameter of 4.5 mm could be 11 mm. Thus, a stent 30' at its nominal fully deployed diameter of 4.5 mm would have a deployed length of 11 min. To assist the interventional physician in placing the stent 30 in a vessel of a human body, the marker bands 26 and 27 will indicate the fully deployed length of the stent 30' that will occur at the final expanded 4.5 mm, nominal diameter of the balloon 25'. If a 3.0 mm nominal diameter balloon angioplasty catheter 20 is selected, the separation distance L2 would (according to FIG. 3) be approximately 14 mm. At an expanded diameter of 4.0 mm, the length L2 for the marker bands 26 and 27 would be set at approximately 12.5 min. It is therefore clearly seen that for each different nominal diameter of a fully expanded balloon, there would be a marker band separation L2 that corresponds to the deployed length of the stent 30 to that specific nominal diameter. For marketing purposes, a manufacturer would have an entire set of balloon angioplasty catheters each with two marker bands whose separation distance L2 would be different for each different nominal balloon diameter. The separation distance L2 would, of course, correspond to the length of the stent when it is deployed to that specific nominal diameter.

FIG. 4 shows another embodiment of this invention which is the stent delivery catheter system 50 which consists of a stent 30, guide wire 40 and balloon angioplasty catheter 55. The balloon angioplasty catheter 55 is identical to the balloon angioplasty catheter 20 of FIG. 1 except the radiopaque marker bands 28 and 29 of the system 50 can be somewhat shorter than the radiopaque marker bands 26 and 27 of system 10. Furthermore, in FIG. 4 the distance L2 is measured from the center line of band 28 to the center line through the band 29.

FIG. 5 shows the system 50 of FIG. 4 with an expanded balloon 25' which causes the deployed stent 30' to be shortened to the length L2.

FIG. 6 shows a stent delivery catheter system 60 which consists of a stent 30, guide wire 40 and balloon angioplasty catheter 65. The balloon angioplasty catheter 65 is identical to the design of FIG. 4 except an additional radiopaque marker band 51 is placed on a distal portion of the inner shaft 23 within the balloon 25. The band 51 is longitudinally positioned to correspond to the position of special balloon expandable cells (not shown) located on the stent 30 near the stent's longitudinal center. Such a cell or cells of the stent 30 have a specific design that allows these cells to be balloon expanded into an essentially circular shape. Thus if that special cell is located at a side branch artery of the main artery into which the stent 30 is placed, then a guide wire (not shown) can be placed through that special cell and into the side branch artery. An expandable balloon can then be placed over the guide wire and into that special cell. The balloon can then be expanded to expand the special cell of the stent 30 thereby allowing blood flow from the main artery into the side branch without any obstruction of the blood flow into the side branch because of a stent wire.

FIG. 7 shows a stent delivery catheter system 70 consisting of a guide wire 40, a stent 35 and a balloon angioplasty catheter 80. The balloon angioplasty catheter 80 has an outer shaft 71, an inner shaft 73, an annular passageway 72 and a balloon 75 onto which is mounted the stent 35. The stent 35 has an undeployed length L3 where L3>L1. When the stent 35 is expanded to its nominal diameter by the balloon 75, it has a deployed length L4 where typically (but not always) L4<L3.

Figure 8:
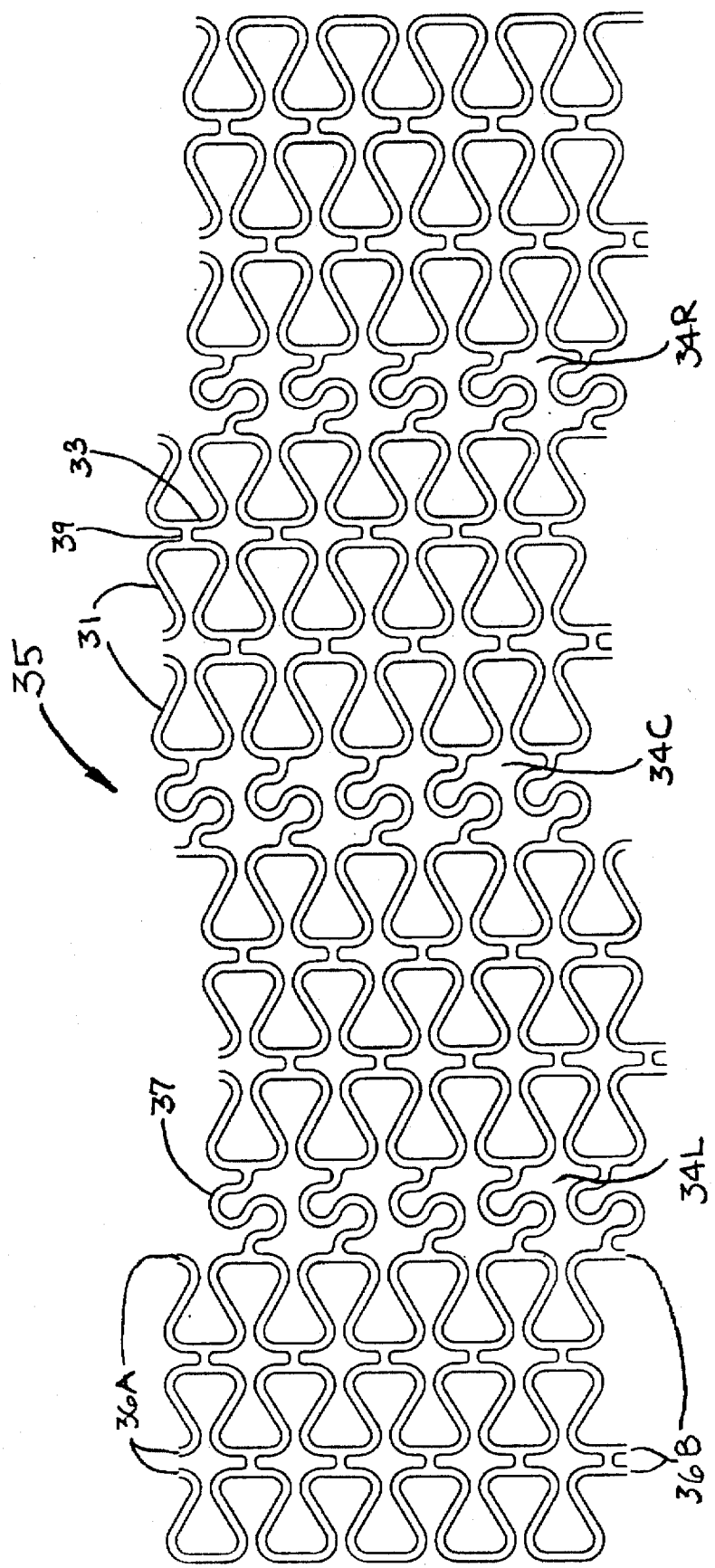
FIG. 8 is a 2-dimensional representation of a stent having three sets of special expandable cells.

FIG. 8 illustrates the stent 35 in its pre-deployed state as it would appear if it were rolled out into a flat, 2-dimensional form. Of course it should be understood that in fact, the stent 35 would actually be in the form of a cylinder both before and after its deployment into a vessel of the human body. The cylindrical form of the stent 35 is accomplished by taking the flat form of FIG. 8 and bending it into a cylinder with all the points 36A being joined to the points 36B. In fact, the stent 35 is typically fabricated by laser machining from a thin-walled, stainless steel cylinder.

FIG. 8 shows that the stent 35 has three sets (or rings) of conventional cells 32, and three sets (or rings) of special expandable cells 34L, 34C and 34R. Each set of cells contains five individual cells. The perimeter length of these cells 34L, 34C and 34R is much longer than the perimeter length of the conventional cells 32. Therefore, when for example one of the cells 34C is placed at a side branch artery and the stent 35 is expanded in the main artery, then an inflatable balloon can be placed within one of the cells 34C and that cell 34C can then be forced into a circular shape by expanding the balloon to a high pressure. Thus any stent structure such as the strut 31 or the strut 33 or the "S" curve 37 can be pushed away from the mouth of the side branch thus allowing blood to flow freely into that side branch with no obstructing structure to impede blood flow.

FIG. 7 shows three radiopaque marker bands 52, 53 and 54 each of which is positioned to indicate respectively the positions of a set of special expandable cells 34L, 34C and 34R of the stent 35 when that stent 35 is fully deployed by the expansion of the balloon 75 to its nominal diameter. Thus the longitudinal position of the radiopaque marker band 52 corresponds to the longitudinal position of the set of cells 34L; the longitudinal position of the radiopaque marker band 53 corresponds to the longitudinal position of the set of cells 34C; and finally, the longitudinal position of the radiopaque marker band 54 corresponds to the longitudinal position of the set of cells 34R. The radiopaque marker bands 52, 53 and 54 could be used with or without the radiopaque marker bands 58 and 59 that indicate respectively the proximal and distal extremities of the stent 35 when it is deployed to its nominal diameter.

Because the stent 35 is considerably longer than the stent 30, there is more than one place along the length of the stent 35 where there are special expandable cells any one or more of which cells can be placed at a side branch artery. This invention envisions one radiopaque marker band located at the site of each such set of special expandable cells of the stent 30 or the stent 35. Although the stent 35 shows three sets of expandable cells 34L, 34C and 34R, it is clearly envisioned that a stent could be made with 1, 2, 4 or 5 of such sets of expandable cells.

Although FIG. 6 shows one central radiopaque marker band 51 and FIG. 7 shows three central radiopaque marker bands 52, 53 and 54, it may also be advantageous to use 2, 4 or 5 radiopaque marker bands to indicate some specific portion of a stent such as, but not limited to, special expandable cells that can be placed at a side branch artery.

Although FIGS. 1, 2, 4, 5, 6 and 7 show balloon expandable stents, it is also anticipated that a stent delivery catheter for a self-expanding stent could also have marker bands that are located so as to correspond to certain sections of such a stent and/or to indicate the deployed length of that self-expanding stent.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A stent delivery catheter having a distal portion and having an inflatable balloon located at the distal portion of the stent delivery catheter, the stent delivery catheter also having an expandable stent releasably attached to the inflatable balloon, the stent delivery catheter also having a proximal radiopaque marker band and a distal radiopaque marker band each fixedly attached to the distal portion of the stent delivery catheter, the longitudinal length between the proximal marker band and the distal marker band being essentially the same length as the length of the stent after the inflatable balloon is inflated to its nominal diameter.

2. The stent delivery catheter and stent of claim 1 wherein each marker band has a proximal end and a distal end, the longitudinal distance between the proximal end of the proximal marker band and the distal end of the distal marker band being essentially the same length as the length of the stent after the inflatable balloon is inflated to its nominal diameter.

3. The stent delivery catheter and stent of claim 1 wherein each marker band has a proximal end and a distal end, and each marker band has a centerline that is halfway between the proximal end and distal end of each marker band, the longitudinal distance between the centerlines of the proximal marker band and the distal marker band being essentially the same length as the length of the stent after the inflatable balloon is inflated to its nominal diameter.

4. The stent delivery catheter and stent of claim 1 wherein the stent includes at least one expandable cell adapted to be placed at a side branch of a main artery and further the expandable cell being adapted to be expanded by means of an inflatable balloon placed through the expandable cell and into the side branch, the stent delivery catheter including one additional radiopaque marker band placed between the proximal and distal radiopaque marker bands, the one additional radiopaque marker band being fixedly attached at the distal portion of the stent delivery catheter so as to be lined up at the same longitudinal position as the longitudinal position of the expandable cell.

5. The stent delivery catheter of claim 4 wherein there are a total of three additional radiopaque marker bands placed between the proximal marker band and the distal marker band, the stent delivery catheter having a first marker band, a second maker band and a third marker band each located at a different longitudinal position at the distal portion of the stent delivery catheter, the stent also having a first expandable cell, a second expandable cell and a third expandable cell with each cell being located at the distal portion of the stent delivery catheter, the first marker band having the same longitudinal position as the first expandable cell, the second marker band having the same longitudinal position as the second expandable cell and the third marker band having the same longitudinal position as the third expandable cell.

6. A set of two or more balloon angioplasty catheters of varying nominal balloon diameters, each balloon angioplasty catheter having a distal portion, each balloon angioplasty catheter also having an inflatable balloon, and a stent releasably attached to the inflatable balloon and two radiopaque marker bands each located at the distal portion of the balloon angioplasty catheter, the separation length between the radiopaque marker bands on each balloon angioplasty catheter being the same length as the length of the stent mounted on that same balloon angioplasty catheter after the stent is deployed by the inflatable balloon to the balloon's nominal diameter.

\* \* \* \* \*